United States Patent [19]
Horn et al.

[11] Patent Number: 5,547,454
[45] Date of Patent: Aug. 20, 1996

[54] ION-INDUCED NUCLEAR RADIOTHERAPY

[75] Inventors: Kevin M. Horn; Barney L. Doyle, both of Albuquerque, N.M.

[73] Assignee: Sandia Corporation, Albuquerque, N.M.

[21] Appl. No.: 147,681

[22] Filed: Nov. 2, 1993

[51] Int. Cl.⁶ .................................................. A61N 5/00
[52] U.S. Cl. ................................................ 600/1; 250/251
[58] Field of Search ............................ 600/1–8; 250/251

[56] References Cited

U.S. PATENT DOCUMENTS

| | | | |
|---|---|---|---|
| 1,466,777 | 9/1923 | Winkelmann | 600/2 |
| 1,720,019 | 7/1929 | Hart . | |
| 1,939,413 | 12/1933 | Robinson . | |
| 3,589,363 | 6/1971 | Banko et al. . | |
| 4,207,874 | 6/1980 | Choy . | |
| 4,781,198 | 11/1988 | Kanabrocki | 128/654 |
| 4,921,327 | 5/1990 | Zito | 600/1 X |
| 4,976,680 | 12/1990 | Hayman | 600/7 |
| 5,295,944 | 3/1994 | Teicher et al. | 600/1 |
| 5,364,336 | 11/1994 | Carr | 600/2 |

OTHER PUBLICATIONS

Horn, K. M., et al., "Micro–Radiosurgery: A New Concept for Radiotherapy Based Upon Low Energy, Ion–Induced Nuclear Reactions," *Nuclear Instruments and Methods in Phys. Res.* B79, pp. 901–906 (1993).

Horn, K M., et al., "Measurement of the Off–Resonance Cross Section of the 6.4 MeV $^1H(^{15}N,\alpha\gamma)^{12}C$ Nuclear Reaction," *Nuclear Instr. and Methods in Phys. Res.* B34 pp. 1–8 (1988).

Kjellberg, R. N., et al., "Stereotactic Bragg Peak Proton Beam Therapy," *Modern Stereotactic Neurosurgery*, pp. 463–470 (1988).

Lyman, J. T., et al., "Charged–Particle Stereotactic Radiosurgery," *Nuclear Instr. and Methods in Phys. Res.*, B10, pp. 1107–1110 (1985).

Moller, W., et al., "A Note on the $^3He+D$ Nuclear–Reaction Cross Section," *Nuclear Instr. and Methods*, vol. 168, pp. 111–114 (1980).

Verhey, L. J., et al., "Proton Beam Therapy," *Ann. Res. Biophys. Bioeng.*, vol. 11, pp. 331–357 (1982).

*Primary Examiner*—Angela D. Sykes
*Attorney, Agent, or Firm*—Dennis Armijo; Gregory A. Cone

[57] ABSTRACT

Ion-induced Nuclear Radiotherapy (INRT) is a technique for conducting radiosurgery and radiotherapy with a very high degree of control over the spatial extent of the irradiated volume and the delivered dose. Based upon the concept that low energy, ion induced atomic and nuclear reactions can be used to produce highly energetic reaction products at the site of a tumor, the INRT technique is implemented through the use of a conduit-needle or tube which conducts a low energy ion beam to a position above or within the intended treatment area. At the end of the conduit-needle or tube is a specially fabricated target which, only when struck by the ion beam, acts as a source of energetic radiation products. The inherent limitations in the energy, and therefore range, of the resulting reaction products limits the spatial extent of irradiation to a pre-defined volume about the point of reaction. Furthermore, since no damage is done to tissue outside this irradiated volume, the delivered dose may be made arbitrarily large. INRT may be used both as a point-source of radiation at the site of a small tumor, or as a topical bath of radiation to broad areas of diseased tissue.

61 Claims, 12 Drawing Sheets

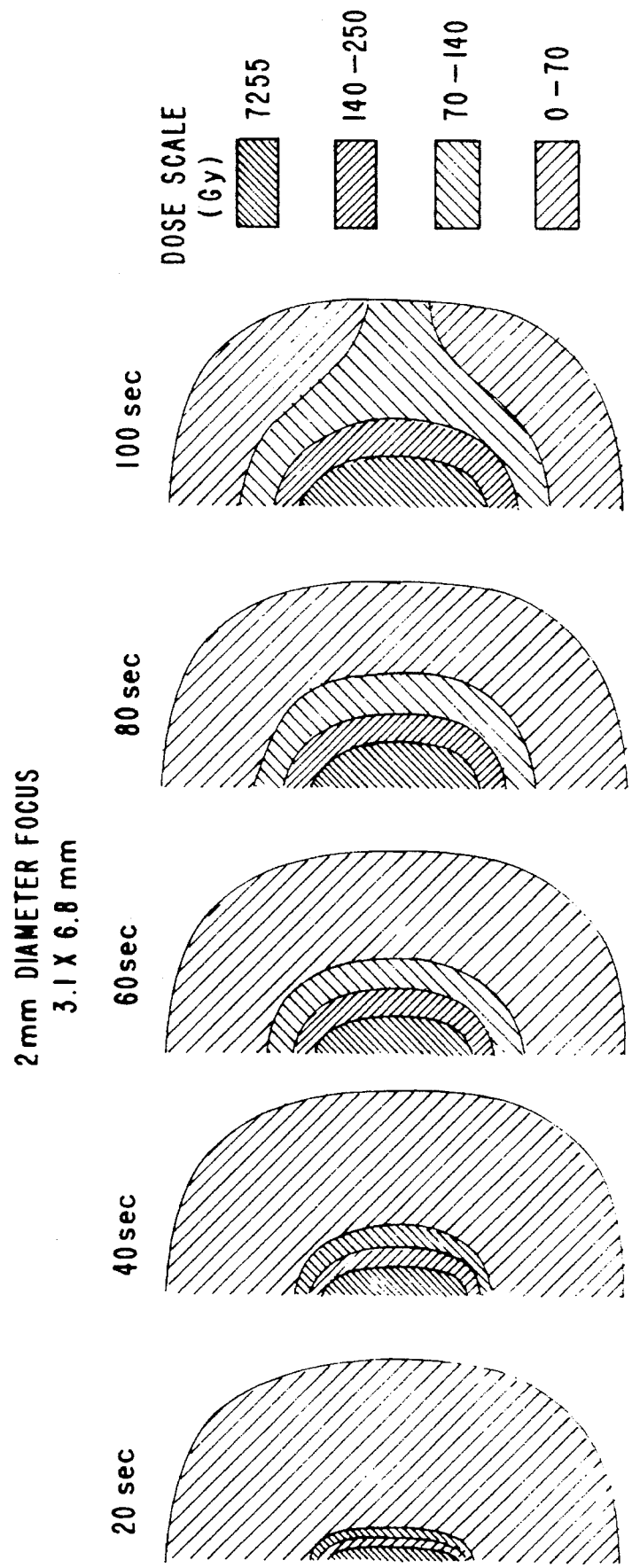

ION-INDUCED NUCLEAR RADIOTHERAPY

GOVERNMENT RIGHTS

The Government has rights to this invention pursuant to Contract No. DE-AC04-76DP00789 awarded by the U.S. Department of Energy.

BACKGROUND OF THE INVENTION

1. Field of the Invention (Technical Field)

The invention relates to the medical application of radiation and more particularly to a method and apparatus for the production via low energy nuclear reactions and delivery of radiation via a conduit-needle or tube to a treatment site.

2. Background Art

Radiotherapy and radiosurgical techniques allow a surgeon to kill diseased tissue in a body with little or no operative intrusions. Ideally, the aim of medical radiation therapy is to deliver a lethal dose of radiation to a clearly defined region of diseased tissue while inflicting little or no radiation damage on surrounding healthy tissue. However, the delivery of radiation to the diseased tissue almost always involves some transport of the incident radiation across healthy tissue which also suffers damage.

The existing techniques for delivering radiation to a region of diseased tissue are proton radiotherapy and radiosurgery, brachitherapy, laser ablation, x-ray irradiation, boron neutron capture therapy (BNCT), electron beam irradiation, gamma-ray knife, and the like.

Proton radiotherapy (PR) delivers radiation to the site of a tumor along a straight-line from outside the body. The incident proton beam interacts directly with the intervening tissue, producing radiation damage along its path to the tumor. Therefore, in many instances, in order to avoid excessive damage to healthy tissue fractionated treatments are necessary, further increasing the cost of treatment and increasing the use of facilities for additional treatment sessions.

The implementation of PR treatments require accelerator facilities to produce the radiation. The 50 to 200 MeV protons necessary for PR are produced by cyclotrons or linacs in facilities costing up to a hundred million dollars and containing significant supporting infrastructure.

The temporary implantation of naturally occurring radioisotope sources at the site of a cancerous tumor, brachitherapy, is also an accepted and frequently used mode of radiation therapy. It entails the insertion of radioactive source material usually in the form of a needle or beads, to the site of a tumor. Once inserted, the source of radiation resides within the body, thus avoiding to a large extent, exposure of healthy tissue to needless irradiation. However, the radiation sources cannot be turned-off, must be stored and handled with extreme care, and exposure geometries and durations must be very accurately determined.

The destruction of cancerous tissue through the use of directed, high-intensity laser light, or laser ablation, is also an existing radiation treatment technique. However, while the laser light can be delivered to the tumor through a flexible conduit, has a self-limiting range of penetration, and poses no danger when turned off, the use of laser irradiation to destroy the tumor also results in scarring of the treated area since there is no opportunity for the re-emergence of healthy tissue. Thus, for dermatological applications, laser treatment of the tumor often results in permanent damage to the appearance and/or function of the host organ.

A significant advantage inherent in proton or deuterium radiotherapy arises from the enhanced radiation doses that can be achieved at a tumor site when the beam energy is tuned so that the ions come to rest at or near the tumor. This enhancement, which is simply a consequence of the position of the Bragg peak (i.e., the maximum) in the proton or deuterium stopping power curve shown in FIG. 1, is a considerable improvement over dose distributions achievable with x-ray or electron irradiations. Unfortunately, the damage done along the incident path of the beam, while much reduced using deuterium or proton beams, can still be as much as 30% of that delivered to the site of a tumor and therefore contributes to the production of damage in healthy tissue. This incidental radiation damage can, at best, limit the deliverable dose for any one exposure, thus requiring repeated treatments at sub-lethal doses so that the damaged healthy tissue can recover before the next treatment, and at worst, can result in the destruction of healthy tissue. It has been noted that large tumors are less likely to be cured at doses of radiation that are still within the tolerance of adjacent normal tissue. Normal tissue sparing is enhanced when (a) the volume of irradiated normal tissue is reduced and (b) the biologic effect on tumor cells is greater than that on surrounding normal cells. These two factors must be optimized to improve the probability of an uncomplicated cure.

By using the products of low energy, ion-induced nuclear reactions for radiation therapy applications, namely ion-induced nuclear radiotherapy or INRT, these factors can be optimized so as to allow arbitrarily large doses of radiation to be delivered, in a single exposure, to a highly localized region of tissue, while inflicting little or no collateral damage on surrounding healthy tissue. Such a form of radiosurgery with clear, pre-defined dose boundaries provides increased precision in controlling the irradiated region and removes many existing constraints on the deliverable dose.

U.S. Pat. No. 1,720,019 to Hart describes a device for transmission of ultraviolet (UV) radiation produced by an external source into the interior of a living body via a liquid medium held in a tube inserted into the body. The tube may also be used to inject the same liquid medium into the area under treatment. Although, Hart indicates all forms of radioactive energy can be used, the description is limited to UV radiation. The Hart device uses the incident radiation itself for destroying living tissue and not the by-products of low energy, nuclear reactions created at the end of the tube to produce the radiation. Finally, Hart's UV radiation is limited to destroying tissue in the line of sight of the inserted device.

U.S. Pat. No. 1,939,413 to Robinson, describes a device specifically intended to irradiate the interior surface of the urethra and bladder with ultraviolet light. Additionally, there are provision made for the draining and injection of fluids into the bladder. The short comings of Hart are also present in this device, in that the UV radiation is limited to destroying tissue also in the line of sight of the device. Additionally, there is no disclosure for the use of a combination of a radiation and thermal treatment to destroy diseased tissue.

U.S. Pat. No. 3,589,353 to Banko et al describes a hollow, ultrasonic vibration device intended to break up and remove animal tissue. In Banko, physical contact between the rapidly vibrating tip and the target tissue results in disintegration of the target material into minute particles which are then flushed from the operating region by fluid from the device tip and suctioned away by another tube within the device tip. Banko does not disclose the deposition of energy via charge particle radiation and heat to destroy diseased tissue.

U.S. Pat. No. 4,207,874 to Choy describes a device intended to clear up obstructions in tubes using a bundled arrangement of optical fibers to provide illumination, imaging and laser ablation of obstructions in its path, and a hollow suction tube to clear the ablated material from the tube. Choy discloses a laser beam propagated down a solid optical fiber to the intended target. Choy further discloses a method to create localized heating and vaporization of obstructing tissue. The only tissue that is destroyed is the tissue that is directly in the laser's path. Choy also does not disclose irradiating and destroying tissue in a volume defined by the range and angular-dependence of the emitted charged particles from a nuclear reaction.

U.S. Pat. No. 4,781,198 to Kanabrocki describes a device to facilitate the accurate positioning of a biopsy needle within a body. The device relies on coating the tip region of a biopsy needle with a gamma-ray emitting material which can be viewed in real time on a scintillation scope during the positioning of the needle. The Kanabrocki device is solely intended for positioning the biopsy needle and does not serve a therapeutic purpose.

U.S. Pat. No. 4,976,680 to Hayman describes a device to facilitate the accurate positioning of radioisotope sources within a body so as to deliver maximized radiation doses to a tumor while minimizing both the exposure of healthy tissue and related surgical procedures in handling the radioactive sources. The apparatus relies upon the use of a set of hollow tubes which are inserted into the patient, terminating in and around the tumor area. Radioisotope sources, in the forms of wires, are then guided down the tubes to the appropriate positions within the tubes in order to deliver maximum radiation dose to the tumor with a minimized dose to healthy tissue. This is a modified form of brachitherapy in which the radioactive source material is not directly handled by the surgeon, but is rather positioned along a fixed path defined by the inserted tubes.

SUMMARY OF THE INVENTION (DISCLOSURE OF THE INVENTION)

In accordance with the present invention there is provided an apparatus and method for the production via low energy nuclear and atomic reactions and delivery of radiation for radiotherapy/radiosurgery.

The preferred apparatus for ion-induced atomic and nuclear reaction-based radiotherapy comprises a conduit, a transmission window within the conduit, target material nuclei inside the conduit, and an apparatus for exposing target material nuclei to ion beams for producing a reaction product for exposure to a predetermined volume.

The preferred conduit and transmission window comprise a material to minimize ancillary nuclear reactions. The preferred conduit further comprises a wall for stopping the ion beams and also comprises a vacuum.

The preferred transmission window is positioned at an end of the conduit. An alternative transmission window is removable from the conduit.

The preferred target material nuclei is affixed to the transmission window. The preferred target material nuclei also comprises a coating on the transmission window. The transmission window and the target material nuclei are preferably oriented to control a dose pattern of the reaction product.

The preferred target material nuclei comprises a thickness to maximize flux and energy of the reaction product and comprises a material permeated with target nuclei.

The target material nuclei can also be independent of the transmission window. The preferred target material nuclei is positioned to direct the reaction product.

An alternative apparatus comprises removing ion beam exposure heat. The conduit can comprise a first conduit and a second conduit. The preferred second conduit is rotatable around a generation point of the reaction product.

The second conduit can also comprise structure for adjusting its length. The second conduit can also comprise a variable aperture on an end of the second conduit.

The transmission window can also be positioned within the second conduit. The preferred second conduit comprises it being evacuated. The second conduit alternatively can be filled with a gas.

The target material nuclei can be affixed to a joint between the first and second conduit.

The preferred target material nuclei comprises deuterium. The preferred target material nuclei also comprises refractory metal deuterides. The preferred refractory metal deuterides comprises a member selected from the group consisting of deuterides, erbium, scandium, titanium, vanadium, and tantalum.

The preferred thickness of the deuterium is between approximately 0.1 and 100 microns.

The preferred ion beam comprises an isotope that maximizes the reaction product. The preferred isotope comprises energy between approximately 0.1 and 2 MeV.

The preferred ion beam comprises an isotope selected from the group consisting of hydrogen, helium and lithium.

The preferred isotope comprises $^3$He. The preferred $^3$He comprises energy between approximately 0.1 and 1 MeV.

The preferred reaction product comprises a member selected from the group consisting of energetic protons, gamma-rays, x-rays, neutrons, alpha particles, heavy ions, electrons and combinations thereof.

The method of the invention is preferably practiced in ion induced atomic and nuclear reaction-based radiotherapy, and comprises providing a conduit, providing a transmission window within the conduit for terminating a vacuum, providing a target material nuclei within the conduit, exposing the target material nuclei to an ion beam transmitted within the conduit, producing a reaction product from exposure of the target material nuclei to the ion beam and exposing a predetermined volume to the transmitted reaction product.

The preferred steps of providing a conduit and a transmission window comprise providing a material to minimize ancillary nuclear reactions. The preferred step of providing a conduit comprises the steps of providing a wall for stopping the ion beams and providing a vacuum.

The preferred step of providing a transmission window comprises positioning the transmission window at an end of the conduit. The alternative step of providing a transmission window comprises providing a removable transmission window.

The preferred step of providing target material nuclei comprises affixing the target material nuclei to the transmission window. The preferred step of affixing target material nuclei comprises coating the target material nuclei on the transmission window.

The steps of providing a transmission window and target material nuclei preferably comprise orienting the transmission window and target material nuclei to control a dose pattern of the reaction product.

The preferred step of providing target material nuclei comprises providing target material nuclei with a thickness sufficient to maximize flux and energy of the reaction product. The preferred step of providing target material nuclei also comprises permeating a material with target nuclei.

The step of providing target material nuclei alternatively comprises providing target material nuclei independent of the transmission window. The preferred step of providing target material nuclei also comprises positioning the target material nuclei to direct the reaction product.

An alterative method also comprises the step of removing heat from the ion beam exposure.

The step of providing a conduit alternatively comprises providing a first conduit and a second conduit. The step of providing a second conduit further comprises rotating the second conduit around a generation point of the reaction product. The step of providing a second conduit further comprises the step of adjusting a length of the second conduit. The step of providing a second conduit alternatively comprises the step of varying an aperture on an end of the second conduit.

The preferred step of providing a second conduit comprises locating the transmission window within the second conduit. The method can further comprise the step of providing a vacuum in the second conduit.

An alternative method of providing a second conduit comprises filling the second conduit with a gas. The alternative method can further comprise the step of affixing the target material nuclei to a joint between the first and second conduit.

The preferred step of providing target material nuclei comprises providing deuterium. The preferred step of providing target material nuclei also comprises providing refractory metal deuterides. The preferred step of providing refractory metal deuterides comprises providing a member selected from the group consisting of deuterides, erbium, scandium, titanium, vanadium, and tantalum.

The preferred step of providing deuterium comprises providing a thickness between approximately 0.1 and 100 microns.

The preferred producing step comprises the step of providing an isotope that maximizes the reaction product. The preferred step of providing an isotope comprises providing energy between approximately 0.1 and 2 MeV.

The preferred producing step also comprises the step of providing an isotope selected from the group consisting of hydrogen, helium and lithium. The preferred step of providing an isotope comprises providing $^3$He. The preferred step of providing $^3$He comprises providing $^3$He with energy between approximately 0.1 and 1 MeV.

The preferred producing step comprises the step of producing reaction products selected from the group consisting of energetic protons, gamma-rays, x-rays, neutrons, alpha particles, heavy ions, electrons and combinations thereof.

The preferred method for ion-induced atomic and nuclear reaction-based radiosurgery comprises targeting a treatment volume, calculating a radiation dose for the volume, inserting the apparatus of claim 1 into a body to a preselected location and providing an ion beam to the apparatus of claim 1 for a predetermined time period.

A primary object of the present invention is to provide a localized mode of ion radiosurgery/radiotherapy.

Another object of the present invention is to provide an easily positioned and less expensive mode of radiosurgery/radiotherapy.

Yet another object of the present invention is to provide a low energy, ion beam-induced exothermic nuclear reaction at or near a specially-tipped needle or tubes placed in the proximity of the treatment area.

A primary advantage of the present invention is that it provides superior localization to existing radiosurgical/radiotherapy apparatus and methods.

Another advantage of the present invention is that it provides maximum radiation exposure to the treatment area while minimizing undesired exposure to the surrounding area.

Yet another advantage of the present invention is that it is smaller and less expensive than existing modalities.

Yet another advantage of the present invention is that it minimizes radioactive mixed waste.

Yet another advantage of the present invention is that it minimizes the requirement for fractionated treatments.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by use of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

Figure 1:
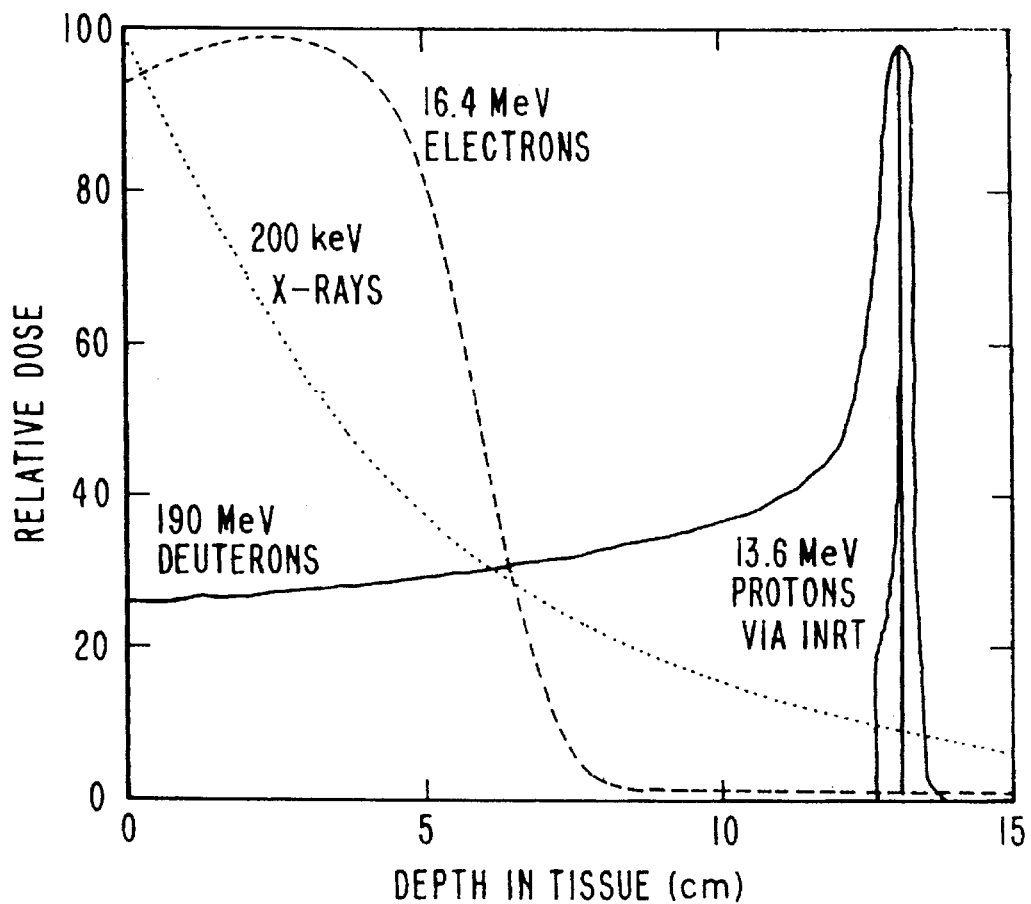
FIG. 1 is a graph of energy deposition versus depth for several forms of radiation including x-rays, electrons, and deuterons (protons) which are commonly used in the clinical environment and shows the same information using the preferred conduit-needle.
Figure 2:
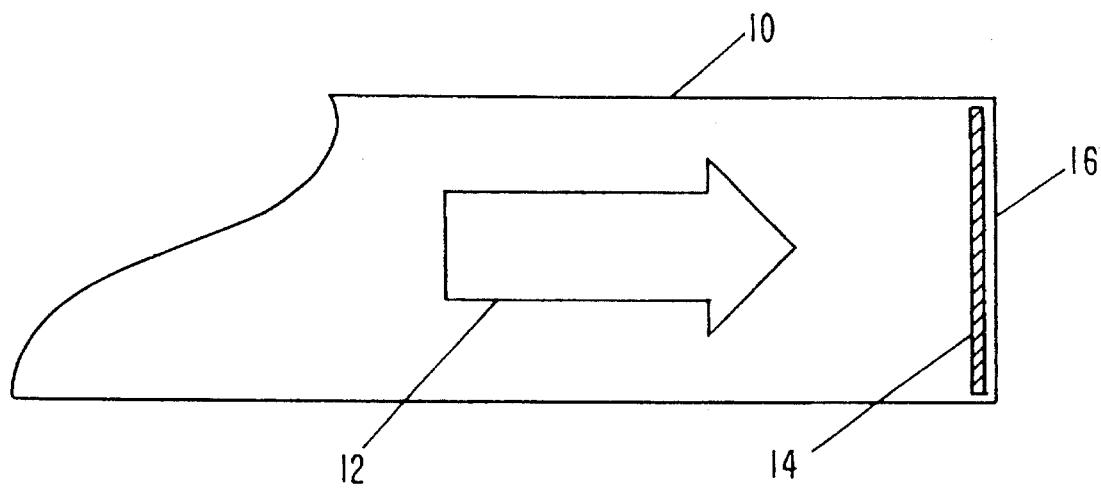
FIG. 2 is a cross sectional view of the preferred conduit-needle.

Traditionally, proton radiotherapy has required the use of high energy proton beams (50–200 MeV) which can penetrate into a patient's body to the site of a tumor that is to be destroyed through irradiation. However, substantial damage is still done to healthy tissue along the path of the incident proton beam, as much as 30% of that done at the tumor site as shown in FIG. 1. An apparatus and method for the production and delivery of energetic reaction products for use in medical radiotherapy, based upon the fact that low energy, ion-induced nuclear reactions can produce radiation products suitable for use in radiotherapy applications, is presented. A general conduit-needle approach or µINRT, 10 as illustrated in FIG. 2, delivers beams of energetic ions 12 to selected target materials 14 coating the inside surface of the needle transmission window 16. Ion beam-induced nuclear reactions are generated at needle tip 16, emitting reaction-specific radiation products 18 directly at tumor site 20. For example, the energetic protons (up to 17.4 MeV) produced by the d($^3$He,p)$^4$He nuclear reaction can be used to deliver a lethal dose (70 Gy) of radiation to a 6.2 millimeter diameter hemisphere of tissue in only 100 seconds using a 1 microamp, 800 keV $^3$He ion beam. The present invention uses low energy, ion-induced nuclear reactions allowing the utilization of comparatively inexpensive, compact, low-energy ion accelerators for proton radiotherapy and minimizes unintended radiation damage to healthy tissue by providing much greater precision in controlling the irradiated volume.

Figure 3:
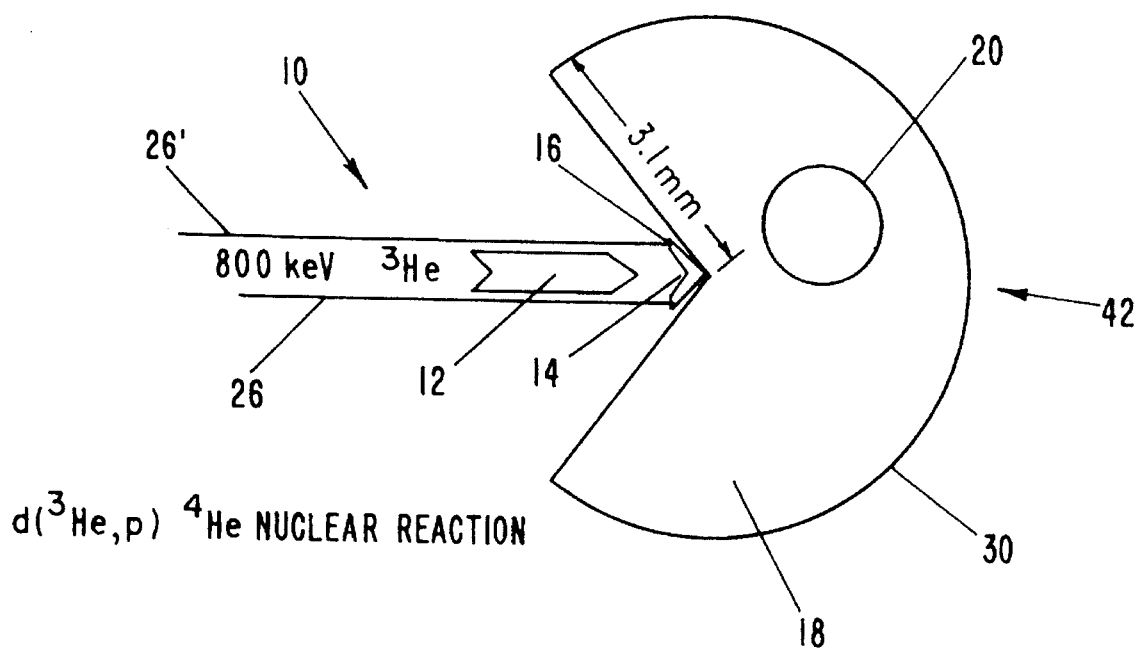
FIG. 3 depicts the preferred method of utilizing the conduit-needle.

A schematic representation of the preferred ion-induced nuclear radiotherapy method and apparatus specifically for proton µINRT is shown in FIG. 3. Evacuated narrow tube (conduit-needle) 10 is employed to deliver beam of energetic ions 12 to specific target material 14 on transmission window at end of needle 16. The configuration of needle transmission window can be tailored to achieve a variety of geometries for the resultant radiation pattern 18. The end of the conduit-needle may be blunt to achieve a forward-directed pattern, or sharply slanted to achieve a sideward-directed pattern. Conduit needle 10 can be inserted in the same manner that a biopsy needle is inserted into a patient to sample a tumor. An ion beam 12 is then directed down evacuated conduit-needle 10 where it strikes the target material 14. The interaction of ion beam 12 with target material 14 results in the generation of selected nuclear reactions at tip of needle 16 which emit reaction-specific radiation products 18 that can include energetic protons, gamma-rays, x-rays, neutrons, alpha particles, or heavy ions which escape from needle-conduit 10 through transmission window 16. These reaction products 18, chosen for their energy and range of penetration, constitute a point-source of radiation at the tumor or treatment site 20. The incident low energy ion beam 12 is stopped in needle walls 26 and 26'. The spatial extent of the irradiated volume is governed by the range of the reaction products. Since the reaction products are confined to a pre-determined region 30 about tip of conduit-needle 16, by virtue of their energy and range in tissue, the deliverable dose is not limited by the generation of incidental damage in surrounding healthy tissue.

Fabrication of the conduit needle assembly is achieved in several steps. Each step is comprised of activities well known to practitioners within each field of activity. For the purpose of clarity and detail, the process will be described for the conduit needles constructed for use with the d($^3$H, p)$^4$He nuclear reaction. The use of other radiation producing nuclear reactions entails the use of other target film materials of perhaps different thickness.

Construction of the conduit needle begins with the selection of hypodermic-grade needle stock and thin stainless steel sheet metal that will serve as the transmission window. The selection of the needle diameter is dependent upon the intended application. Topical INRT (i.e., broad area, external irradiations) may be performed with a 1" diameter needle; µINRT (i.e., point-source applications) requiring insertion of the final conduit needle into a body could use hypodermic needle stock as small as no. 19 STD gauge (approximately 1 mm outer diameter). The needle stock is cut to the appropriate length for its intended purpose and the end is prepared for welding according to standards known to practitioners of the art. The thickness of the metal sheet to be used as the transmission window is selected to minimize its thickness (in order to induce the least energy degradation in the product radiation) while still maintaining sufficient mechanical strength to sustain the load of air pressure which it encounters when the needle conduit is evacuated. For the example of the smallest conduit needle, illustrated in FIG. 12, the type 304 stainless steel transmission window has a thickness of 127 microns; the wall thickness of the hypodermic needle is 178 microns. The maximum range of the incident 800 keV $^3$He ions is only 1.6 microns in stainless steel. Thus, the design ensures that none of the incident radiation can escape the conduit needle interior.

The transmission window is sized to the dimensions of the selected needle stock and then cleaned in preparation for deposition of the target thin film. The cleaning procedures involve techniques well known to practitioners of the art and result in a surface free of contaminants, irregularities or mechanical flaws. A mask is applied to the inner surface of the transmission window in order to prevent deposition of the target film on the rim of the transmission window, which will be involved in the actual weld joint with the needle stock. Use of the mask helps insure the integrity and purity of the weld joint by preventing the inclusion of extraneous target film materials into the weld bead. For the specific nuclear reaction cited for proton generation (i.e., d($^3$He, p)$^4$He, the process for depositing a thin erbium target layer, which will ultimately contain the deuterium target nuclei, involves the use of a device commonly referred to as an evaporator. In this commercial device, the transmission window is positioned above a heated crucible containing erbium. The evaporator is then evacuated to pressures below $10^{-6}$ Torr, in order to avoid oxidation or contamination of the erbium layer during deposition. The erbium-containing crucible is then heated to beyond the boiling point of its contents which results in gas-phase erbium being emitted from the crucible. Those erbium atoms which are emitted in the direction of the suspended transmission window stick to the cooler surface and accumulate to form a layer whose thickness is determined by the exposure time to the heated crucible. A thin film deposition monitor indicates the deposited layer thickness during the process. For the d($^3$He,p)$^4$He nuclear reaction, an erbium layer thickness of 5 microns is suitable.

After removal from the evaporator, the transmission window with its newly deposited erbium thin film is placed in a gas furnace where it is exposed to deuterium gas at elevated temperatures. This process results in a 5 micron thick deuterated film with a stoichiometry of approximately ErD$_2$, or a deuterium concentration of $1.16 \times 10^{23}$ H/cm$^3$.

Using techniques well known to practitioners of the art, the transmission window, with its deposited film, is then welded to the end of the conduit needle stock, forming a vacuum-tight blank-off. Such small scale welding is accomplished using finely focused electron beams or laser beams that heat the needle/transmission window joint while the needle is rotated below the beam in a rotary fixture. The needle is then leak-checked to insure that a vacuum-tight weld has indeed been attained.

Figure 4:
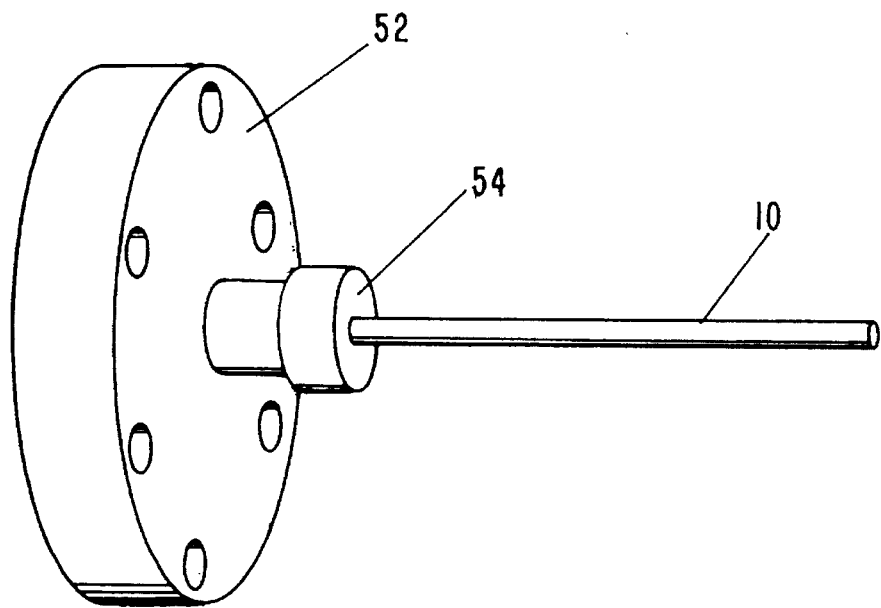
FIG. 4 is a perspective view of the preferred conduit-needle attached to a vacuum flange adapter.
Figure 5:
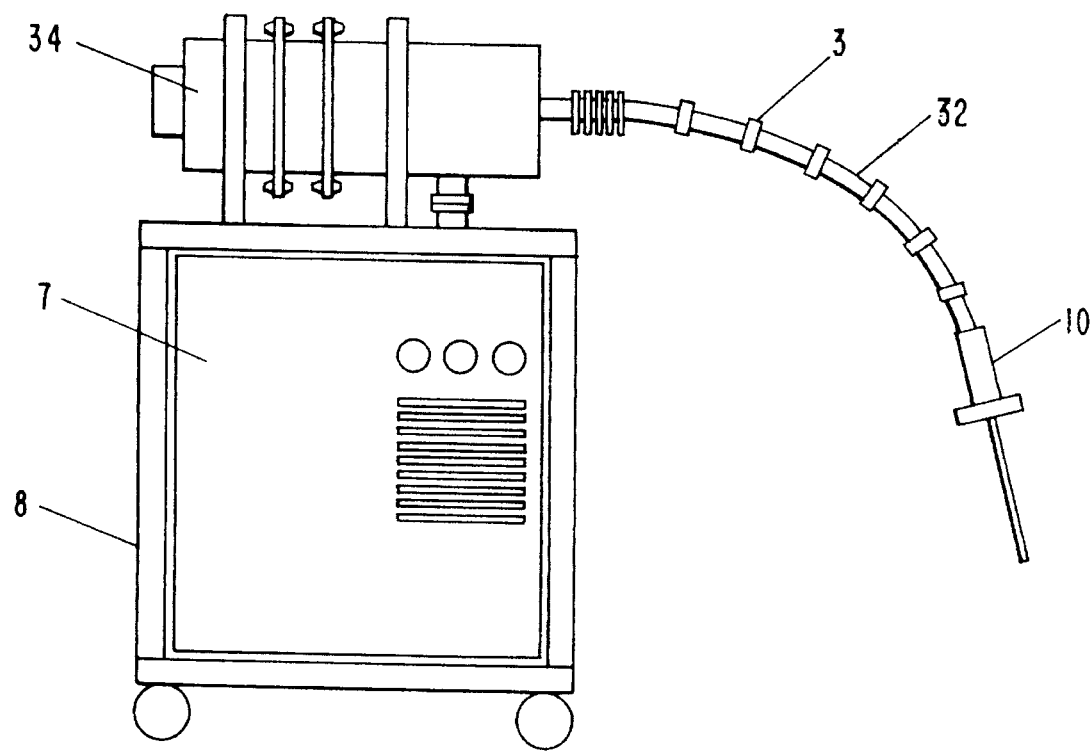
FIG. 5 shows the preferred hardware set up for use of the conduit-needle in the μINRT mode.
Figure 6:
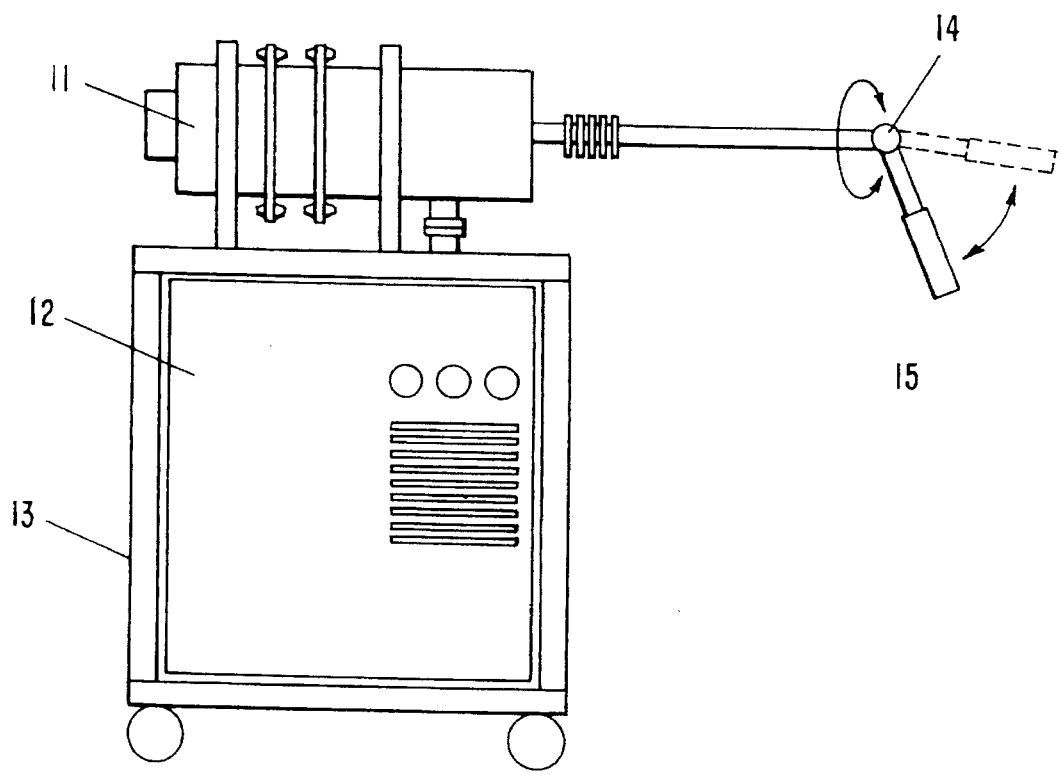
FIG. 6 shows an alternative hardware set up for the use of the conduit-needle in the topical INRT mode.
Figure 7E:
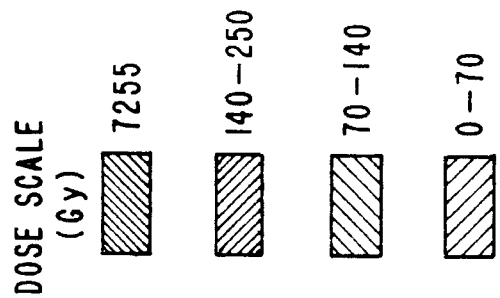
FIG. 7 shows radiation dose maps for various exposure durations using a 1 μA, 800 KeV $^3$He Ion Beam incident on an ErD$_2$ coated transmission window.
Figure 7E:
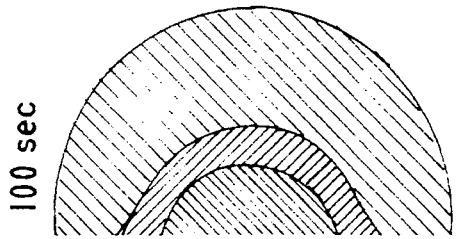
Figure 7D:
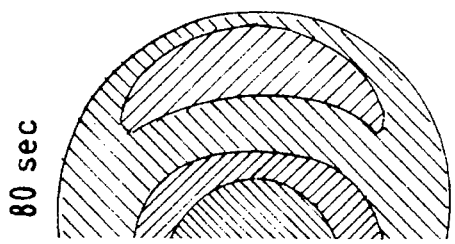
Figure 7C:
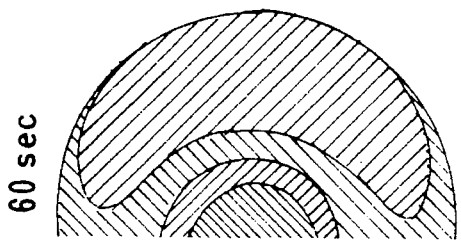
Figure 7B:
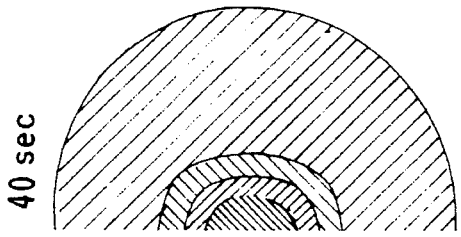
Figure 7A:
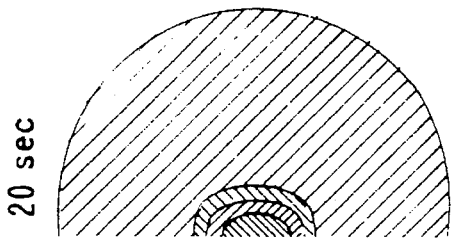

As shown in FIG. 4 completed needle 10 is then mounted in a commercial VCO fitting (or other suitable vacuum fitting) which is itself welded into a standard vacuum flange 52 (such as a 2.75" copper gasket type Conflat flange or 3" O-ring type Dependex flange). A VCO fitting maintains a tight viton O-ring seal to base of the conduit needle 10 providing both physical rigidity and support for needle 10 and the requisite vacuum seal. Flange 52 may then be bolted onto an existing ion accelerator beam line which contains the standard beam steering and alignment diagnostics necessary to deliver an ion beam to its intended target as shown in FIGS. 5 and 6. In this specific example, delivery of the $^3$He ion beam to the needle target then results in the production of the therapeutic radiation.

In practice, the target tumor would initially be detected through an advanced diagnostic technique, several of which are well known in the art, at a very early stage of development. The exact location of the tumor could then be pinpointed with one or more scanning methods, such as nuclear magnetic resonance imaging, computer-aided tomography, or another high resolution imaging technique and the most benign conduit-needle insertion vector to the tumor would be determined. The axis of ion beam 12 and the insertion vector would then be made coincident either by appropriately orienting the patient in a three-axis positioning frame (as is currently done for proton radiotherapy) or by adjusting the orientation of ion beam 12. As shown in FIG. 5, a jointed, evacuated tube 32 consisting of a series of small, quadrupole magnetic lenses 38 could be used to provide a flexible, hand-held delivery "ion-hose" for use by a surgeon. Such a delivery system is the functional equivalent of a radiation "airbrush" for medical applications. In the alternative, a small, single stage radio frequency quadrupole (RFQ) 34 can prove sufficiently compact to allow the entire accelerator assembly to be oriented on its own three-axis frame. The very last step in targeting conduit-needle 10, in some cases, may include the incorporation of an endoscope to visually acquire target tumor (not shown) just before commencing irradiation.

A number of factors must be considered when deciding which of numerous low energy nuclear reactions are suitable candidates for use in radiation therapy applications. Among the criteria to be considered are the incident ion energy required to produce the nuclear reaction, the energy, range and species of the products of the nuclear reaction, and the manner in which these products will lose their energy to the target.

The preferred reaction for the production of energetic protons for radiotherapy applications is the d($^3$He,p)$^4$He reaction In this reaction, an incident $^3$He nucleus with an energy of 650 keV collides with a deuterium nucleus producing the natural isotope of helium, $^4$He, and a proton with an energy of up to 17.4 MeV. A continuous beam of $^3$He ions incident on a deuterium-bearing target produces a point-source of energetic protons that irradiates the surrounding tissue.

The total yield of energetic protons from the ion-induced nuclear reaction can be given in its most simple form in the thin target approximation as, $$Y = N_i \cdot \rho(x) \cdot \sigma(E) \tag{1}$$

where $N_i$ is the number of incident ions, $\rho(x)$ is the density of reaction nuclei in the target and $\sigma(E)$ is the reaction's energy-dependent total cross section. Since the reaction's cross section varies with energy, and the energy of the incident ions change with depth into the target material, the yield can best be thought of as arising from a series of thin target slabs, dx, in each of which the energy of the ion and the reaction cross section are constant. The energy of the incident $^3$He ions at any depth in the target can be determined from stopping power tables, so the energy dependence of the reaction cross section can be re-caste as a depth dependence, yielding, $$Y = N_i \rho \int_0^{\text{end of range}} \sigma(x) dx \tag{2}$$

The limits of the integration reflect the range of penetration of the incident $^3$He ions into target material 14. $N_i$, the total number of incident $^3$He ions is a constant which is factored out of the integrand, as is the deuterium concentration, $\rho(x)$, when dealing with a uniformly deuterated target film. The number of incident ions, $N_i$, is usually measured in terms of the total electrical charge deposited on the target by the ion beam. For a beam of singly-ionized $^3$He ions, $N_i$ is simply the total charge collected on the target divided by the charge per ion ($1.6 \times 10^{-19}$ Coulombs). A 1 microCoulomb (μC) ion exposure therefore corresponds to $N_i = 6.25 \times 10^{12}$ incident $^3$He nuclei.

K. M. Horn and W. A. Lanford, *Nucl. Instr. and Meth.* B34 (1988) pp. 1–8, have shown that for the fabrication of hydrated titanium films, that hydrogen (and therefore deuterium) concentrations of $1.16 \times 10^{23}$ deuterium/cm$^3$ can be attained in titanium films. Similar deuterium concentrations have been attained in other stable matrices such as erbium and scandium, among others.

A very reliable measurement of the total cross section for the d($^3$He,p)$^4$He nuclear reaction is reported for $^3$He energies up to 2.5 MeV by Möller and Besenbacher, Möller and F. Besenbacher, *Nucl. Instr. and Meth.* 168 (1980) pp. 111–114. The cross section for this reaction is quite broad with a peak of 0.825 barn at about 650 keV. Stipulating an incident $^3$He ion energy of 800 keV (in order to increase the thick target proton yield) and a TiD$_2$ target, the energy-dependent cross section curve can be converted to its corresponding depth-dependent cross section curve. Using the 800 keV $^3$He ion's range of 1.9 microns in TiD$_2$ as the upper limit of integration, the integral in equation 2 can be evaluated numerically, yielding a value of $6.7 \times 10^{-29}$ cm$^3$.

Substituting these values into equation 2, the total yield of 17.4 MeV protons resulting from a 1 μC exposure of a TiD$_2$ transmission window to an 800 keV $^3$He ion beam is calculated to be, $$Y = 4.85 \times 10^7 \text{ protons/μC } ^3\text{He.} \tag{3}$$

The delivered dose can quickly be estimated in the following manner. Since 17.4 MeV protons have a range of 3.1 millimeters in tissue, the total extent of the proton-irradiated region is simply a sphere of 6.2 mm diameter, or a "treatment" volume of 0.3 cm$^3$. All of the kinetic energy of each 17.4 MeV proton must be deposited within this spherical volume, therefore, the total radiation dose delivered to this volume by each proton is easily estimated. Using the definition of a rad as the amount of energy imparted to matter by ionizing particles per unit mass of irradiated material, the total delivered radiation dose per proton to the treatment volume is:

$$\text{Dose} = \frac{\text{Energy}}{\text{mass}} = \frac{E}{\rho \cdot V} \quad (4)$$

Thus for a 17.4 MeV proton, a tissue density of 1.0 g/cm$^3$, and an irradiated treatment volume of 0.3 cm$^3$, the calculated radiation dose per proton is 9.3×10$^{-7}$ rads/proton. The overall rate of irradiation is simply the product of this result and the rate of proton production per µC of incident $^3$He beam, calculated in expression (3). The total irradiation rate calculated for the stated conditions using the d($^3$He,p)$^4$He reaction is 45.1 rads/µC. Thus, for a 1.5 microamp $^3$He ion beam directed onto a TiD$_2$ target, a 100 second exposure would be required in order to deliver a lethal 70 Gy dose of radiation to the treatment volume. The fixed initial energy of the reaction products insures that the radiation exposure will not extend beyond the limits of the treatment volume.

This, however, neglects both the 1/r$^2$ dependence of the energy deposition and also the end-of-range Bragg peak in the proton stopping power curve. The results of a more refined calculation of the delivered radiation dose using a computer-based simulation of the proton energy loss through individual volume elements of the treatment area is shown in FIG. 7. These results also illustrate the time evolution of the radiation damage pattern for two separate source geometries. The upper row of patterns represent the radiation fields obtained for an incident $^3$He beam which is focused to a point at the end of the needle—producing a true point-source of radiation. The lower row of field patterns were produced assuming a $^3$He beam 12 which is spread over a 2 mm spot at end of the needle—producing a more extended source. The increased area for the production of energetic protons at the needle tip results in an increase in the radiation pattern size from 3.1×4.8 mm to 3.1×6.8 mm. Moreover, the effects of the 1/r$^2$ dependence of the deposited dose and the enhanced Bragg peak at the end of range for the proton are explicitly illustrated in this computer-generated dose calculation.

Figure 8:
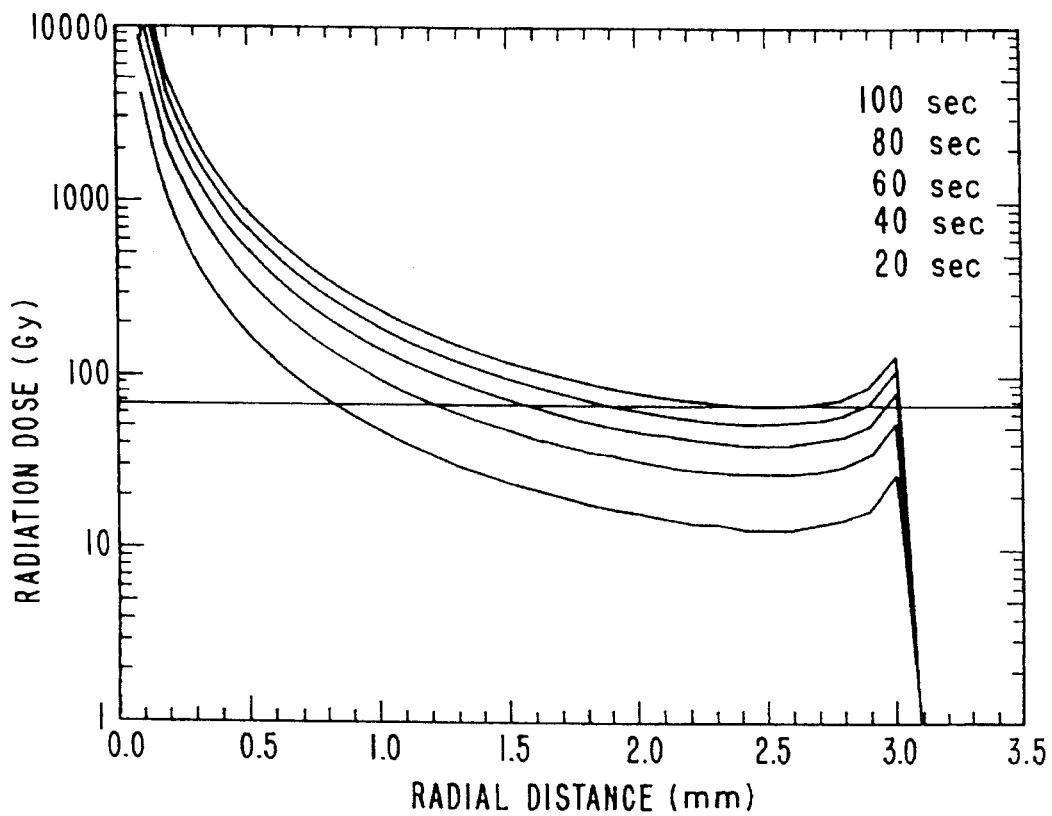
FIG. 8 is a graph of the accumulation of radiation damages for the conditions cited in FIG. 7.

The relationship between delivered dose, distance from the needle tip, and exposure time is presented graphically in FIG. 8. Again, the effects of the 1/r$^2$ dependence and enhanced end-of-range dose (due to the Bragg peak) are evident. Moreover, it is seen that exposures as short as 20 seconds deliver a minimum of 15 Gy to the entire treatment volume.

The spatial extent of the treatment volume can be further increased by orienting the target material and transmission window within the conduit-needle so as to maintain an angle of 45° with the conduit-needle axis. Upon exposure to a point-focused ion beam, this obliquely oriented transmission window allows the resulting radiation to expose areas directly to the side of the conduit-needle up to the full range of the reaction products. Subsequent rotation of the conduit-needle allows the radiation pattern to be swept through a full 2π, thus exposing a volume of tissue whose dimensions are the full range of the reaction products in the forward direction and twice the range of the reaction products in the lateral direction. Use of the obliquely oriented target with an extended ion beam focus further broadens the exposure volume.

Figure 9:
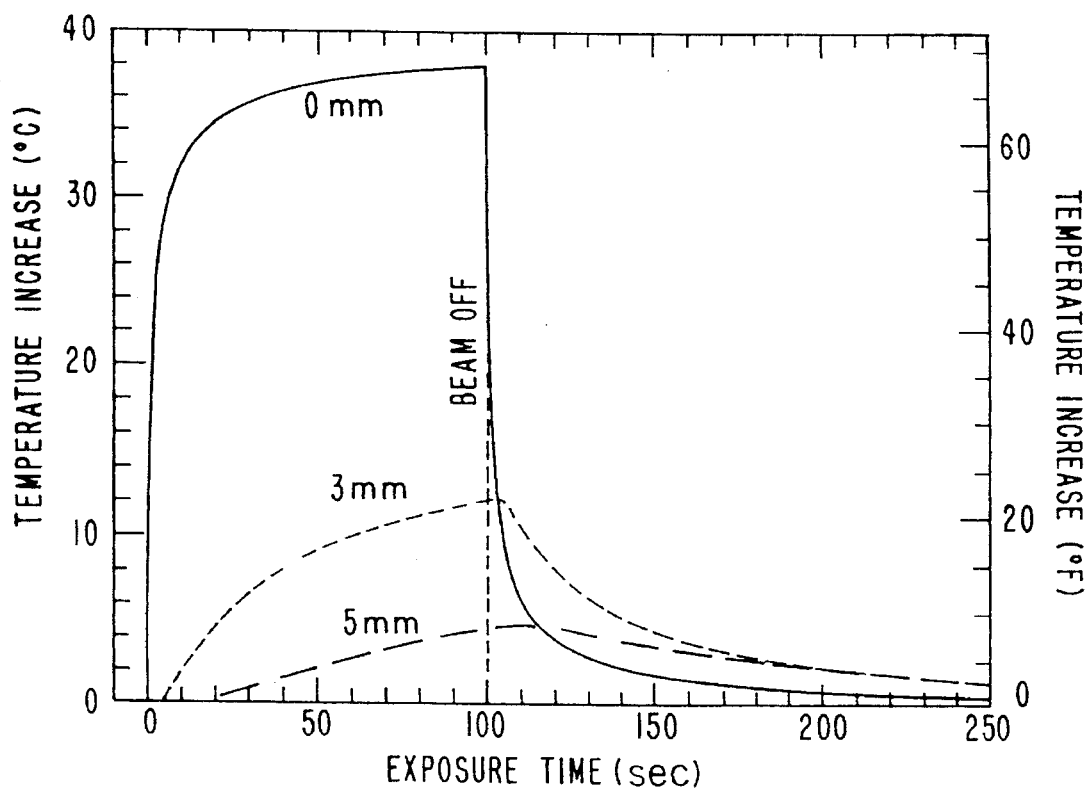
FIG. 9 is a graph of heat generation during radiation delivery for the conditions cited in FIG. 7.

Dissipation of heat produced by the incident $^3$He ion beam impacting the target material is also a concern in evaluating possible collateral damage to surrounding healthy tissue. For the purpose of determining the local temperature rise due to this technique, the heat transfer process is approximated by considering the treatment area as imbedded in a large mass with the same stoichiometry and thermal conductivity as muscle tissue. Heat, (corresponding to the stopping of the $^3$He ion beam in the needle transmission window), is introduced continuously over a 100 second exposure time at the center of this volume and removed only by conduction through the medium. For the specific conditions used in the preceding dose calculation for the d($^3$He, p)$^4$He reaction, the temperature at the outer boundary of the irradiated volume will increase by approximately 12° C. during the 70 Gy exposure and decrease to less than a 5° C. elevation in temperature above ambient within 40 seconds after the end of the exposure. This calculation, however, excludes heat removal by the conduit-needle and the local circulatory system (not shown); thus, it is an upper-bound. The temperature increase above ambient, due to the radiation delivery is shown graphically in FIG. 9. It might also be noted that moderate elevation of the local temperature in and around the tumor may be a desirable effect. It has been observed that the elevation of temperature increases the radiosensitivity of tumors; after one hour of heating at 43° C., the radiosensitivity of certain tumors has increased by factors of 3 to 4. Thus, the heat generated by the INRT technique may be useful in enhancing its effectiveness.

Medical radiation treatments kill cancerous tumors through exposure to either low LET (linear energy transfer) radiation such as x-rays, brehmstahlung and gamma rays, or exposure to high LET radiation such as protons and heavy ions. The effect of the radiation exposure on a tumor and its surrounding tissue depends critically on the mechanism of the energy deposition and also on the response of the exposed tissue to the irradiation.

Figure 10:
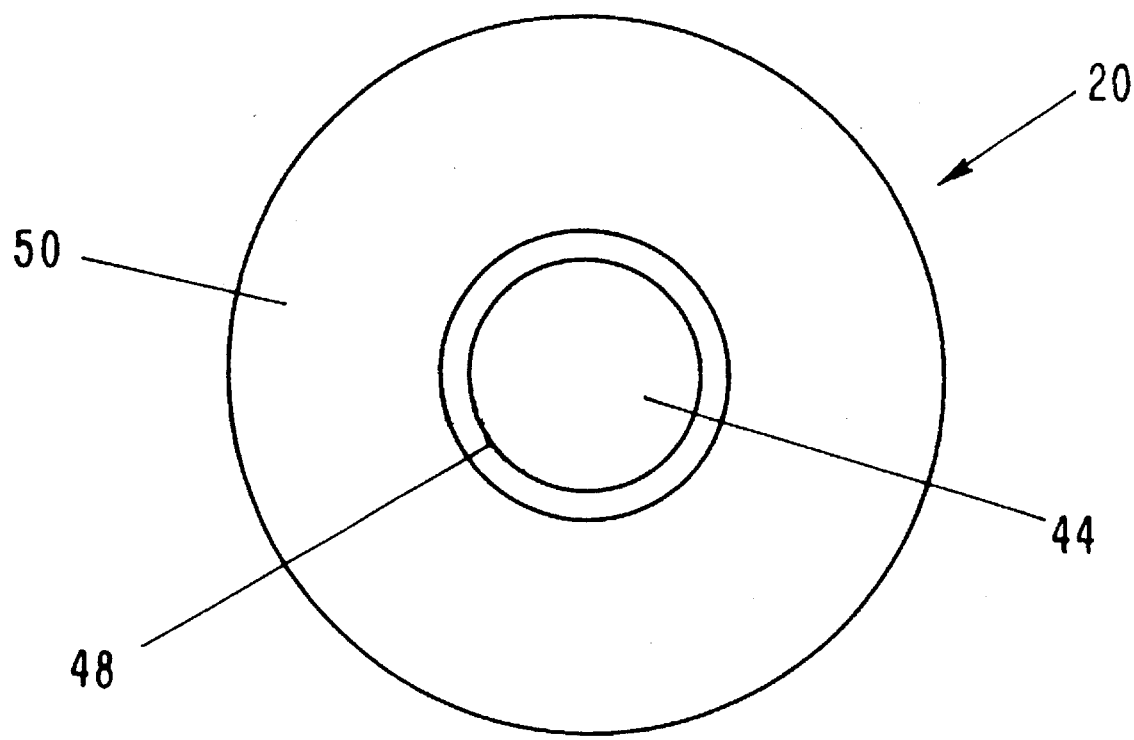
FIG. 10 is a drawing of the typical structure of a cancerous tumor in the early stages of development (i.e. >0.4 mm diameter)

Cancer cells proliferate in a disordered fashion and at a rate which exceeds the growth of blood vessels. As a result of this, it has been observed in human bronchial carcinomas that tumors larger than 400 microns in diameter actually consist of three distinct layers (as shown in FIG. 10). The core of the tumor 44, with the least access to oxygen-rich blood vessels, consists of dead (necrotic) cells. Surrounding this dead, inner core 44 is a layer of dormant, inactive cells (hypoxic cells) 48 which are insufficiently supplied with oxygen and therefore metabolize at a much lower rate than amply nourished cancer cells. The outer-most layer of the tumor is made up of well-oxygenated and nourished cancer cells 50. It has also been empirically observed that hypoxic cells 48 are three times less radiosensitive to low LET radiation than cancer cells 50 in the outer, oxygen-rich layer. As a consequence of this fact, low LET radiation treatments designed to deliver a lethal radiation dose to active cancer cells 50 of the tumor 20, while still maintaining a sub-lethal exposure in the surrounding healthy tissue, can prove insufficient to kill hypoxic cells 48. If not destroyed, surviving hypoxic cells 48 gain access to oxygen and nutrients no longer being absorbed by the dead outer layer and ultimately revive tumor 20. Failure to completely destroy all the cells within tumor 20 results in its reoccurrence.

Figure 11:
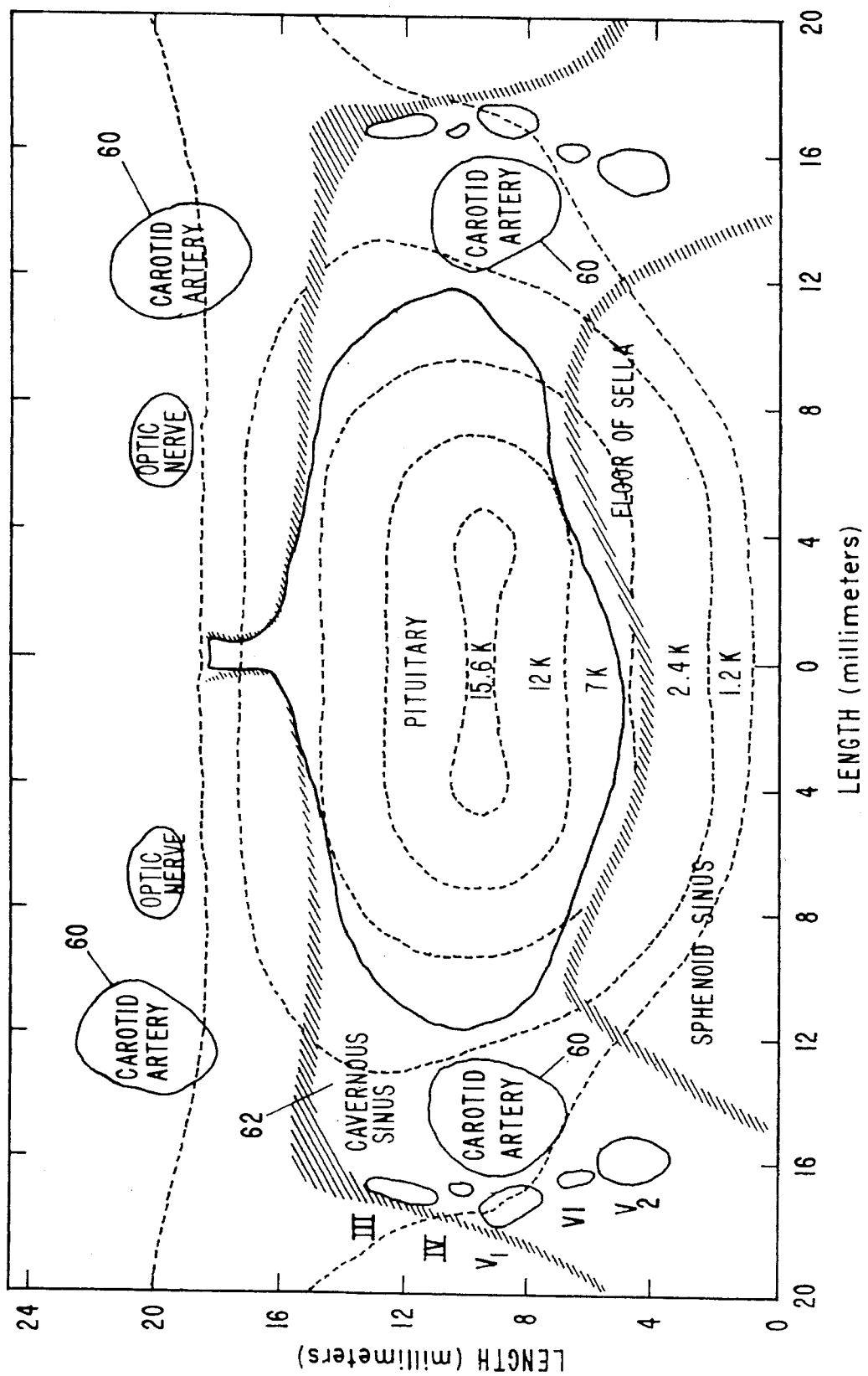
FIG. 11 is an isodose curve for a 15.6 krad radiation exposure of a pituitary gland using traditional stereotactic proton radiotherapy treatments.

No such difference in radiosensitivity is observed during exposures to high LET radiation; in this respect, high LET radiation is more effective in killing the entire tumor. However, high LET radiation, including proton beams, still produce significant damage in healthy tissue along the path of the incident beam. This, in turn, limits the amount of radiation that can be delivered along a single incident path in a single treatment session. Current proton radiotherapy techniques accommodate this constraint by separating radiation treatments in time (fractionating the treatments) and by using different incident beam paths which intersect at the tumor, in order to spare healthy tissue. However, this separation in time and space (i.e. ion path) increases the cost and complexity of the treatment and can still result in exposure levels to surrounding healthy tissue in excess of any desirable level. The size of the biological structures around a typical irradiation target and the degree of exposure currently endured by surrounding tissue is illustrated in FIG. 11, from R. N. Kjellberg and M. Abe, *Modern Stereotactic Neurosurgery*, edited by L. D. Lunsford (Martinus Nijhoff Publishing, Boston, 1988), p. 468, which displays an isodose curve for a 15.6 krad proton radiotherapy treatment of a pituitary gland. This exposure was performed using 12 separate incident beam paths (portals) with a 7 mm proton beam; 12 portals is considered an atypically large number. While almost the entire pituitary gland was successfully exposed to at least 7 krad of radiation, the patient's carotid arteries 60 and cavernous sinus 62 received between 1.2 and 2.4 krad of collateral damage from this treatment. From the length scale of FIG. 11, the increased precision possible with a 6.1 millimeter diameter irradiation volume is apparent.

The successful use of radiation in destroying diseased tissue relies critically upon the ability to localize the damage created by the exposure. In this context, traditional proton radiotherapy has been proven to be a significant advance in delivering enhanced doses of radiation to surgically inaccessible tumors. The present invention which uses low energy, ion-induced nuclear reactions attains even higher localization of the radiation exposure.

Figure 12:
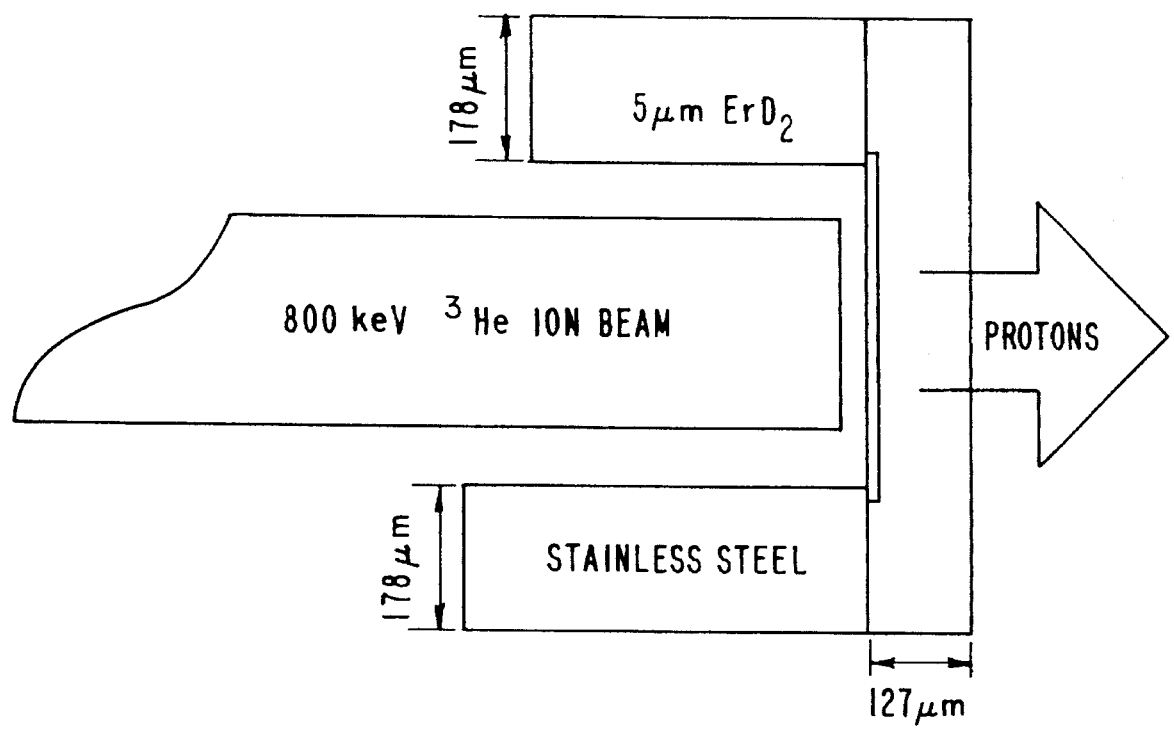
FIG. 12 shows the range of incident ions and product radiations in a typical µINRT hypodermic needle using the 650 keV d($^3$He,p)$^4$He nuclear reactor.

The present apparatus and method are significant improvements over existing technologies because once needle 10 is inserted into the site of a tumor 20, the deliverable radiation dose at tumor 20 is not constrained by the additional radiation damage to healthy tissue 42 outside the range of the reaction products. Therefore, fractionated treatments can be avoided, significantly reducing costs and facility use. Further, the introduction and production of all other radiations are contained completely within the needle-conduit 10, as shown in FIG. 12. The facilities required for the present invention produce a wide range of nuclear reaction products with sub-MeV ion beams produced by accelerators, or radio frequency quadrupoles, that are small, comparatively inexpensive and have modest requirements with respect to structural shielding. Little, if any, radiation need be produced in generating a low energy ion beam, and high energy radiation is produced at the transmission window only when the ion beam is directed to conduit needle 10. Target material 14 is, in effect, a switchable point source of radiation that is turned on or off by the presence of the ion beam 12. No radioactive waste is produced and no medical personnel need handle or be exposed to radioactive material.

Proton radiotherapy relies solely on the use of protons to deliver the radiation exposure. Ion-induced nuclear radiotherapy (INRT) provides more flexibility in the form of radiation that can be generated (i.e. protons, gamma rays, heavy ions, neutrons, x-rays) since the reaction products are controlled by the combination of target material 14 and ion beam 12 which are used. The most significant difference in the two techniques resides in the precision with which the radiation exposure can be controlled. PR is typically used to produce exposures on a scale of centimeters. Indeed, for the treatment of many advanced tumors this is exactly the scale needed. However, as the ability to detect certain forms of cancer through blood chemistry testing and ultrasound testing advances, tumors will be identified for treatment at earlier stages of their development and will therefore be smaller in size. The precise nature of the INRT technique will allow a millimeter-size tumor to be destroyed with certainty, while minimizing the risk to surrounding healthy tissue.

Given the highly localized nature of the INRT technique, and its flexibility of application, several clinical applications are possible.

The INRT needle can be used to expose small, localized tumors to lethal doses of radiation in a single treatment session. Tumors located in surgically inaccessible and/or delicate locations would be prime candidates for INRT exposures. This category of tumors would be typified by vocal chord lesions which are not easily treatable with surgery or laser ablation without risking permanent alteration or loss of voice. This embodiment is shown schematically in FIG. 5.

In contrast to the preferred embodiment of the INRT technique, which makes use of slender, needle-like conduits inserted directly to the site of a tumor, the alternative embodiment of the INRT technique is used to irradiate broad areas of tissue with a near-uniform dose of radiation. In this embodiment, termed "topical INRT" broad area or scanned ion beams are transmitted down a large diameter (one inch, typically) tube where they ultimately strike the target material, which will produce the desired nuclear reaction. In this "scaled-up" version of INRT, the end of the conduit-tube remains external to the patient's body and therefore, a physical separation exists between the end of the conduit-tube and the subject to be treated. The presence of this gap eliminates any thermal contact between the transmission window of the conduit-tube and the patient.

In the presence of such a gap, the ion beam current delivered to the target material can be increased several thousand-fold over that used in μINRT, (thus exceeding milliamp beam current), and thereby produce much larger radiation doses. This increased radiation yield, however, is counter-balanced by the fact that the conduit-tube is not internal to the body and thus, not all the product radiation of the nuclear reaction is delivered to the patient. Nonetheless, this circumstance gives rise to several favorable conditions for external or topical radiation treatments. First, the resulting radiation dose incident on the patient is much more spatially uniform over the entire extent of the exposure. Second, in the absence of thermal contact between the patient and the conduit-tube, ion beam currents in excess of milliamps can be delivered to an actively-cooled target material, so that the rate of radiation delivery can be made greater than with μINRT. Thirdly, through the use of apertures and collimators which can block emission of reaction products in certain directions, the broad, uniform radiation field can be customized to conform to a particular shape or exposure pattern.

Displayed in FIG. 6 is a schematic representation of the topical INRT embodiment. In this illustration, a compact radio frequency quadrupole (RFQ) 11, along with its power supply 12, are positioned in a movable stand 13 which allows gross positioning capability for the delivered radiation. The low energy ion beam emitted by the RFQ 11 is directed through the first conduit and into the inter-conduit coupling joint 14 between the fixed, first conduit and the rotatable second conduit. A water-cooled target material within joint 14 is struck by the incident low energy ion beam resulting in nuclear reactions which give rise to the production of radiation. The product radiation which is emitted along the path defined by second conduit 15 is conducted to the site of the therapeutic irradiation. Second conduit 15 is rotatable around the incident beam axis as well as the azimuthal axis. The second conduit may be terminated by a transmission window in which case vacuum is maintained within the second conduit-tube, or the transmission window may be comprised in the inter-conduit joint 14. In the latter case, second conduit 15 may be filled with a selected gas or even just air.

Figure 13:
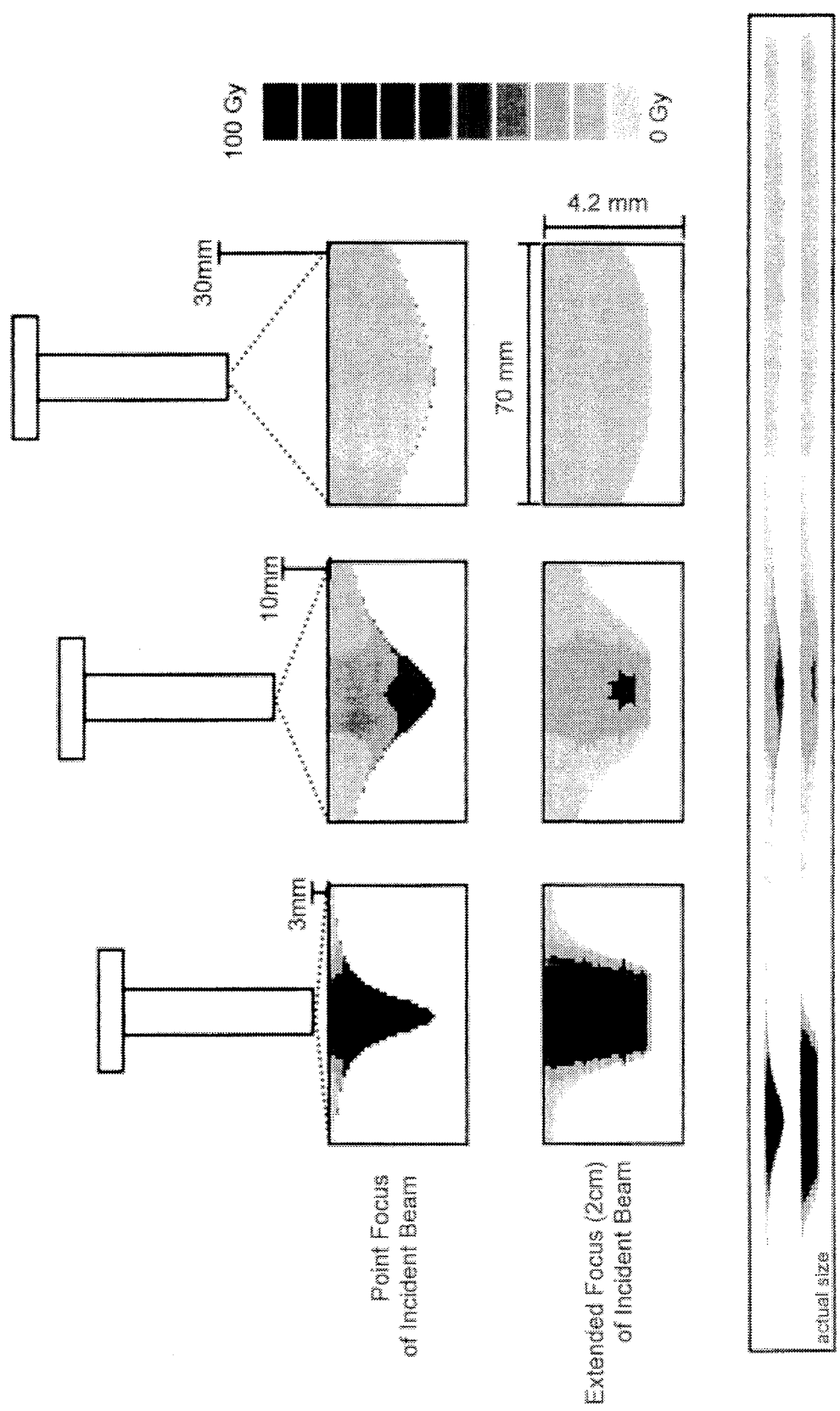
FIG. 13 shows radiation intensity patterns for topical INRT application with needle-to-tissue separations of 3, 10 and 30 mm.

In preparation for use, the RFQ is positioned in proximity to the patient; the appropriate aperturing masks and collimators are placed on the end of second conduit 15, or on the patient. The second conduit-tube is then rotated so as to point at the region of tissue which is to receive the irradiation treatment. Once positioned, the low energy ion beam may be transmitted down the conduit-tubes and irradiation commenced for the requisite time. FIG. 13 depicts the nature and shape of the radiation fields attainable for various conduit-tube patient separations, using this embodiment of the INRT technique.

One application of topical INRT resides is in use as a radiation source that can be brought directly into the surgical operating theater. After the surgical removal of large tumors from within the body, it is often preferred to irradiate the area which surrounded the tumor in order to kill any remaining, isolated cancer cells; such a procedure is called inter-operative radiation therapy (IORT). Currently, IORT procedures usually require that after removal of the tumor, the patient be temporarily sutured and transported to radiation facilities outside the operating room—most often located in the hospital basement for shielding purposes. The additional risk to the patient, scheduling difficulties with the radiation producing equipment, and compounded complexity of the procedure could be vastly reduced if a small, portable radiation source could be brought into the operating room. The INRT technique can provide the surgeon with a roll-away system which can be wheeled into position and used to irradiate the tumor-containing region with protons of fixed penetration range.

Owing to the compactness of the equipment necessary to perform topical INRT, another application involves its use as a technique suitable for use in a doctor's office for dermatological applications. The treatment of skin cancers through the use of fractionated radiation treatments, delivered quickly to the affected region would avoid procedures involving surgical removal or laser ablation, and their ensuing scarring, and also minimize the requirement for elaborate radiation producing equipment. An example of the broad area applications of the INRT technique are illustrated in FIG. 13 where the radiation intensity patterns are shown for needle-to-tissue separations of 3, 10 and 30 mm. In this mode of usage, the retraction of the needle tip from the targeted area results in a widening of the affected area and a smoothing of the radiation pattern. Thus, broad, uniform exposures are attainable for dermatological applications of the INRT technique. Use of pre-selected aperturing cones on the end of the conduit would further allow even the lateral extent of the radiation pattern to be controlled.

Industrial Applicability:

The invention is further illustrated by the following non-limiting example.

EXAMPLE I

Figure 14:
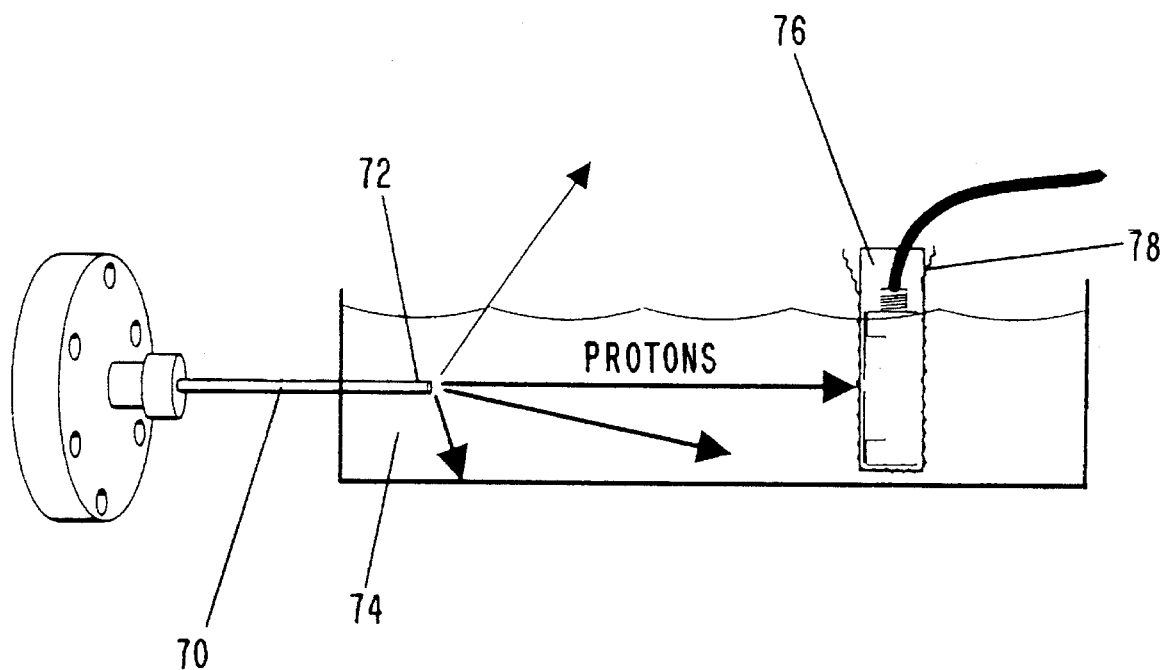
FIG. 14 shows the test set up of Example I.

The validity of the computer calculations was verified experimentally with a prototype INRT system in which the energy deposited (or dose delivered) by energetic protons transmitted through a water medium was measured as shown in the test set up of FIG. 14. Both water and muscle tissue have a density of 1 gm/cm$^3$ and have very similar stopping power effects on energetic protons, therefore, water provides a very suitable substitute target in which measurements of proton energy loss and dose deposition can be easily made. To this end, a test system was constructed in which a solid state, surface barrier detector could be positioned at arbitrary distances from an INRT needle tip within this tissue-like medium. This measurement, schematically shown in FIG. 14 made use of a 0.10" diameter needle-conduit 70 mounted in a VCO fitting on a standard 2.75" Conflat vacuum flange. Tip of needle-conduit 72 was inserted into water bath 74. A surface barrier detector 76, encased in a water-tight aluminum foil "sock" 78, to maintain it's electrical operation in water, was mounted on a calibrated, linear translation stage, and submerged into water bath 74. A tandem Van de Graaff ion accelerator provided the 800 keV $^3$He ion beam used in the measurements; the $^3$He ion beam was directed into the needle conduit using the existing beam handling systems present on the accelerator beam line (not shown).

Figure 15A:
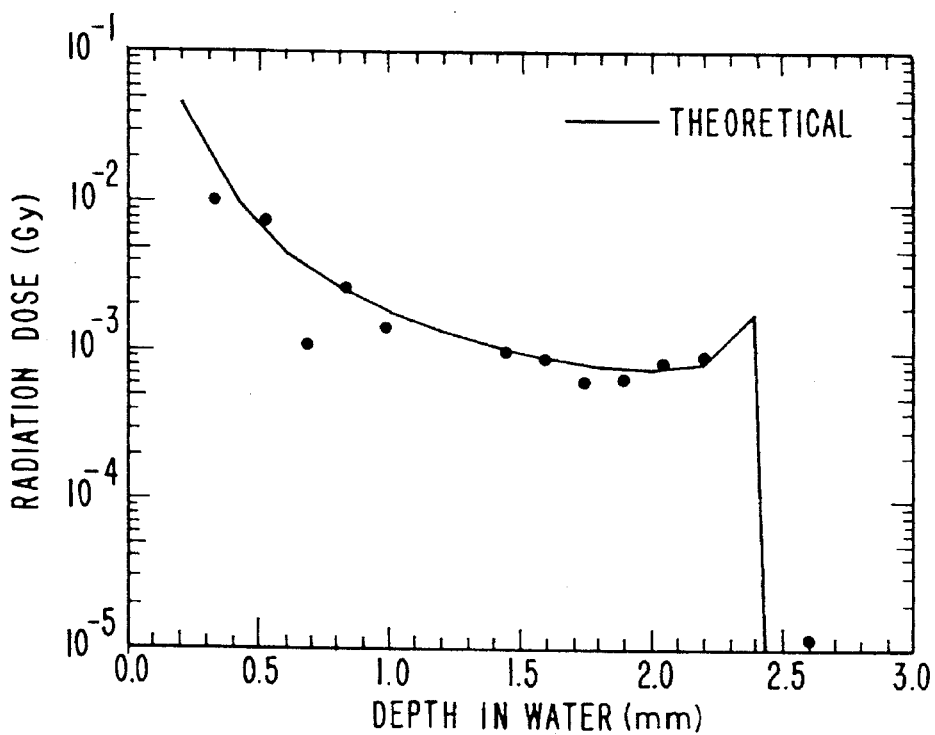
FIG. 15a is a graph of radiation dose vs. depth in water for theoretical values and the test results of Example I.
Figure 15B:
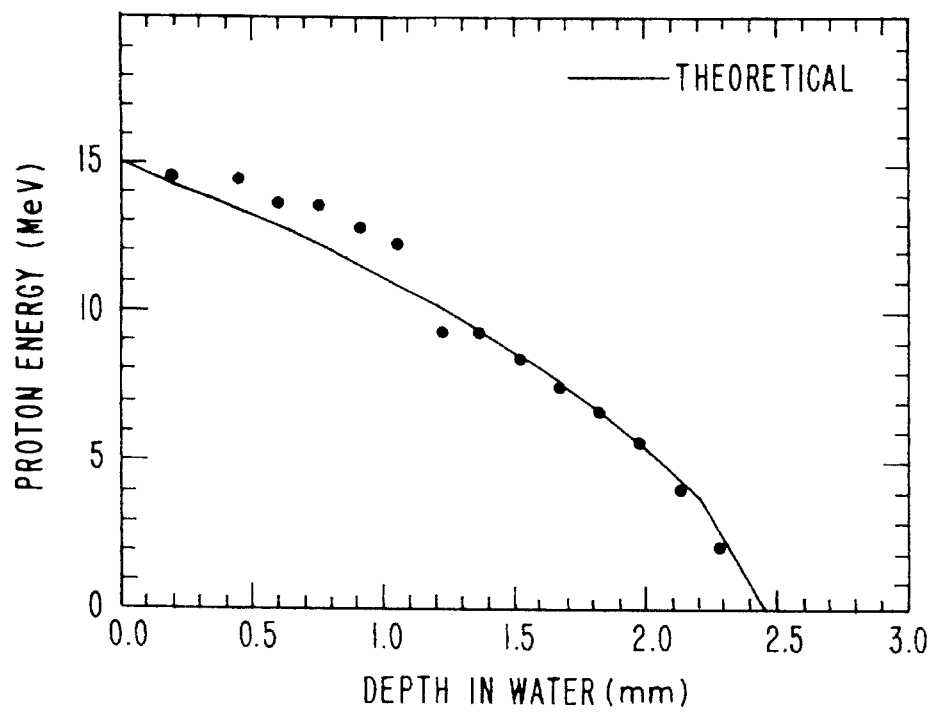
FIG. 15b is a graph of proton energy vs. depth in water for theoretical values and the test results of Example I.

Using the linear translation stage to position the detector at varying distances from the needle-conduit tip, timed measurements were made of the emitted proton yield and energy at each of the measurement positions. The results of the dose versus distance measurement agree almost precisely with the shape of the dose curve predicted by the computer calculation indicating that the $1/r^2$ dependence and enhanced Bragg stopping power peak are correctly reflected in the computer algorithm. Measurement of the proton yield indicated a total range of 2.5 mm into the water. This value is less than the theoretically predicted value of 3.2 mm because of the water-tight aluminum "sock" placed around the detector. The protective aluminum "sock" lessens the energy of the protons before they reach the test detector. Graphs showing the theoretical and actual test measurements are shown in FIGS. 15a and 15b.

The results of these measurements indicate very good agreement between the computer simulation results and the experimentally measured dose.

The preceding example can be repeated with similar success by substituting the generically or specifically described reactants and/or operating conditions of this invention for those used in the preceding example.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. An apparatus for ion-induced atomic and nuclear reaction-based radiotherapy comprising:

means for introducing an ion beam into a conduit means;

conduit means for guiding the ion beam and containing the beam therewithin;

transmission window means at the end of said conduit means distal to the means for introducing an ion beam, said transmission window means containing the beam with the conduit means;

target material nuclei means inside said conduit means; and means for exposing the target material nuclei means to the ion beam for producing a nuclear reaction product for exposure to a predetermined volume external to the conduit.

2. The invention of claim 1 wherein said conduit means and said transmission window means comprise a material to minimize ancillary nuclear reactions.

3. The invention of claim 1 wherein said conduit means comprises vacuum means.

4. The invention of claim 1 wherein said transmission window means is removable from said conduit means.

5. The invention of claim 1 wherein said target material nuclei means is affixed to said transmission window means.

6. The invention of claim 5 wherein said target material nuclei means comprises coating means on said transmission window means.

7. The invention of claim 5 wherein said transmission window means and said target material nuclei means are oriented to control a dose pattern of said reaction product.

8. The invention of claim 5 wherein said target material nuclei means comprises a thickness to maximize flux energy of the reaction product.

9. The invention of claim 1 wherein said target material nuclei means comprises a material permeated with target nuclei.

10. The invention of claim 1 wherein said target material nuclei means is independent of said transmission window means.

11. The invention of claim 10 wherein said target material nuclei means is positioned to direct said reaction product.

12. The invention of claim 10 further comprising means for removing heat from an exposure to said ion beam.

13. The invention of claim 1 wherein said conduit means comprises a first conduit means and a second conduit means.

14. The invention of claim 13 wherein said second conduit means is rotatable around a generation point of said reaction product.

15. The invention of claim 13 wherein said second conduit means comprises adjustable length means.

16. The invention of claim 13 wherein said second conduit means comprises variable aperture means on an end of said second conduit means.

17. The invention of claim 13 wherein said transmission window means is within said second conduit means.

18. The invention of claim 13 wherein said second conduit means comprises vacuum means.

19. The invention of claim 13 wherein said second conduit means is filled with a gas.

20. The invention of claim 13 wherein said target material nuclei means is affixed to a joint means between said first and second conduit means.

21. The invention of claim 1 wherein said target material nuclei means comprises deuterium.

22. The invention of claim 21 wherein said target material nuclei means comprises refractory metal deuterides.

23. The invention of claim 22 wherein said refractory metal deuterides comprises a member selected from the group consisting of deuterides, erbium, scandium, titanium, vanadium, and tantalum.

24. The invention of claim 21 wherein said deuterium comprises a thickness between approximately 0.1 and 100 microns.

25. The invention of claim 1 wherein said ion beam comprises an isotope that maximizes said reaction product.

26. The invention of claim 25 wherein said isotope comprises energy between approximately 0.1 and 2 MeV.

27. The invention of claim 1 wherein said ion beam comprises an isotope selected from the group consisting of hydrogen, helium and lithium.

28. The invention of claim 27 wherein said isotope comprises $^3$He.

29. The invention of claim 28 wherein said $^3$He comprises energy between approximately 0.1 and 1 MeV.

30. The invention of claim 1 wherein said reaction product comprises a member selected from the group consisting of energetic protons, gamma-rays, x-rays, neutrons, alpha particles, heavy ions, electrons and combinations thereof.

31. A method for ion induced atomic and nuclear reaction-based radiotherapy, the method comprising the steps of:

a) providing an ion beam into one end of a conduit;

b) providing a transmission window means at the other end of the conduit for terminating a vacuum and confining the ion beam within the conduit and transmission window means;

c) providing target material nuclei within the conduit;

d) exposing the target material nuclei within the conduit;

e) producing a nuclear reaction product from exposure of the target material nuclei to the ion beam; and f) exposing a predetermined volume to the transmitted reaction product external to the conduit.

32. The method of claim 31 wherein the steps of providing a conduit and a transmission window comprise providing a material to minimize ancillary nuclear reactions.

33. The method of claim 31 wherein the steps of providing an ion beam into one end of a conduit additionally comprises providing a vacuum.

34. The method of claim 31 wherein the step of providing a transmission window comprises providing a removable transmission window.

35. The method of claim 31 wherein the step of providing target material nuclei comprises affixing the target material nuclei to the transmission window.

36. The method of claim 35 wherein the step of affixing target material nuclei comprises coating the target material nuclei on the transmission window.

37. The method of claim 35 further comprising the step of orienting the transmission window and target material nuclei to control a dose pattern of the reaction product.

38. The method of claim 35 wherein the step of providing target material nuclei comprises providing target material nuclei with a thickness sufficient to maximize flux and energy of the reaction product.

39. The method of claim 31 wherein the step of providing target material nuclei comprises permeating a material with target nuclei.

40. The method of claim 31 wherein the step of providing target material nuclei comprises providing target material nuclei independent of the transmission window.

41. The method of claim 40 wherein the step of providing target material nuclei comprises positioning the target material nuclei to direct the reaction product.

42. The method of claim 40 further comprising the step of removing heat from the ion beam exposure.

43. The method of claim 31 wherein the step of providing a conduit comprises providing a first conduit and a second conduit.

44. The method of claim 43 further comprising the step of rotating the second conduit around a generation point of the reaction product.

45. The method of claim 43 further comprising the step of adjusting a length of the second conduit.

46. The method of claim 43 further comprising the step of varying an aperture on an end of the second conduit.

47. The method of claim 43 further comprising the step of locating the transmission window within the second conduit.

48. The method of claim 43 further comprising the step of providing a vacuum in the second conduit.

49. The method of claim 43 further comprising the step of filling the second conduit with a gas.

50. The method of claim 43 further comprising the step of affixing the target material nuclei to a joint between the first and second conduit.

51. The method of claim 31 wherein the step of providing target material nuclei comprises providing deuterium.

52. The method of claim 51 wherein the step of providing target material nuclei comprises providing refractory metal deuterides.

53. The method of claim 52 wherein the step of providing refractory metal deuterides comprises providing a member selected from the group consisting of deuterides, erbium, scandium, titanium, vanadium, and tantalum.

54. The method of claim 51 wherein the step of providing deuterium comprises providing a thickness between approximately 0.1 and 100 microns.

55. The method of claim 31 wherein the producing step comprises the step of providing an isotope that maximizes the reaction product.

56. The method of claim 55 wherein the step of providing an isotope comprises providing energy between approximately 0.1 and 2 MeV.

57. The method of claim 31 wherein the producing step comprises the step of providing an isotope selected from the group consisting of hydrogen, helium and lithium.

58. The method of claim 57 wherein the step of providing an isotope comprises providing $^3$He.

59. The method of claim 58 wherein the step of providing $^3$He comprises providing $^3$He with energy between approximately 0.1 and 1 MeV.

60. The method of claim 31 wherein the producing step comprises the step of producing reaction products selected from the group consisting of energetic protons, gamma-rays, x-rays, neutrons, alpha particles, heavy ions, electrons and combinations thereof.

61. A method for ion-induced atomic and nuclear reaction-based radiosurgery, the method comprising the steps of:
   a) targeting a treatment volume;
   b) calculating a radiation dose for the volume;
   c) inserting the apparatus of claim 1 into a body to a preselected location;
   d) providing an ion beam to the apparatus of claim 1 for a predetermined time period.

* * * * *